US009517196B2

(12) United States Patent
Smigel et al.

(10) Patent No.: US 9,517,196 B2
(45) Date of Patent: Dec. 13, 2016

(54) LIP BALM

(71) Applicants: Robell Research, New York, NY (US); Aeran Kerie Ha, Reseda, CA (US)

(72) Inventors: Lucia Smigel, New York, NY (US); Tammy Ha, Reseda, CA (US)

( * ) Notice: Subject to any disclaimer, the term of this patent is extended or adjusted under 35 U.S.C. 154(b) by 783 days.

(21) Appl. No.: 13/911,478

(22) Filed: Jun. 6, 2013

(65) Prior Publication Data

US 2013/0330427 A1 Dec. 12, 2013

Related U.S. Application Data

(60) Provisional application No. 61/656,131, filed on Jun. 6, 2012.

(51) Int. Cl.

| | | |
|---|---|---|
| *A01N 65/00* | (2009.01) | |
| *A61K 8/97* | (2006.01) | |
| *A61K 8/19* | (2006.01) | |
| *A61K 8/92* | (2006.01) | |
| *A61K 8/68* | (2006.01) | |
| *A61K 8/73* | (2006.01) | |
| *A61K 8/65* | (2006.01) | |
| *A61Q 19/00* | (2006.01) | |
| *A61K 8/26* | (2006.01) | |

(52) U.S. Cl.
CPC . *A61K 8/97* (2013.01); *A61K 8/19* (2013.01); *A61K 8/26* (2013.01); *A61K 8/65* (2013.01); *A61K 8/68* (2013.01); *A61K 8/735* (2013.01); *A61K 8/92* (2013.01); *A61K 8/922* (2013.01); *A61K 8/927* (2013.01); *A61Q 19/001* (2013.01)

(58) Field of Classification Search
CPC ..................................................... A61K 36/00
USPC ......................................................... 424/725
See application file for complete search history.

(56) References Cited

U.S. PATENT DOCUMENTS

| | | |
|---|---|---|
| 5,395,620 A | 3/1995 | Huc et al. |
| 5,420,248 A | 5/1995 | Devictor et al. |
| 5,476,671 A | 12/1995 | Cho et al. |
| 5,622,656 A | 4/1997 | Huc et al. |
| 6,660,281 B1 | 12/2003 | Nakanishi et al. |
| 2010/0286102 A1 | 11/2010 | Vielhaber |
| 2012/0189684 A1 | 7/2012 | Buckley et al. |

OTHER PUBLICATIONS

Boswellin CG product information from Sabinsa Corporation (5 pages).
Boswellic Acid, Wikipedia; http:/en.wikipedia.org/wiki/Boswellic_acid (accessed Mar. 19, 2013).
Hirulip Product information from Lipotec; Jun. 2010 (9 pages).
Marine Filli9ng Spheres Product Information from BASF (7 pages) (Mar. 2008).
Symrepair product information from Symrise. (14 pages).
Volulip product information from Sederma (2009).
MSDS for Dow Corning 2503 Cosmetic Wax (9 pages) (Feb. 14, 2009).
Ceramides; Chemistry, Occurence, Biology and Analysis; The AOCS Lipid Library, http://lipidlibrary.aocs.org/lipids/ceramide/index.htm (7 pages) updated Feb. 7, 2013.
Lintner et al; The effect of a synthetic ceramide-2 on transepidermal water loss after stripping or sodium lauryl sulfate treatment: an in vivo study; International Journal of Cosmetic Science 19, 15-25 (1997).

*Primary Examiner* — Michael Meller
(74) *Attorney, Agent, or Firm* — Grace J. Fishel

(57) ABSTRACT

A lip balm product having a synthetic ceramide, an anti-irritant compound, sodium hyaluronate, cosmetic wax, boswellic acids and/or esters and/or salts thereof, extract of the *Portuluca pilosa* plant, matrikin-mimetic peptide, dehydrated microspheres of marine collagen and glycosaminoglycans, and mica along with optional lip balm formulation acceptable carriers and/or solvents. Where desired, the lip balm may further contain medicinal agents suitable for the treatment of various conditions of the lip.

2 Claims, No Drawings

LIP BALM

This application claims priority of U.S. Provisional Patent Application Ser. No. 61/656,131, filed Jun. 6, 2012.

FIELD OF INVENTION

The invention relates to the field of topical lip balms and use thereof to aid in the moisturization of lips and in (a) helping to heal and (b) helping to prevent cracking of the lips. The invention also relates to the field of cosmetic lip balms that aid in giving the lips a smoother and/or plumper look and feel.

BACKGROUND OF THE INVENTION

Lips are the most susceptible to dryness and cracking of any part of the skin. Topical lip balm products such as the present invention protect and help restore lips from the effect of dryness and cracking. Lips are continuously moving and subjected to repeated stress (ultraviolet radiation, dry air, etc.). The lip area is fragile by nature and needs protection in order to overcome the deficiency, or gradual decline of dermal macromolecules. Naturally dry through the fineness of the barrier and absence of moisturizing and lipid restoring glands, the vermilion of the lips is continuously subjected to drying. The mechanisms resulting in moisturization have to be strengthened to limit chapping and cracking. The vermilion of the lips is devoid of sebaceous and sweats glands. Unlike the skin, the lips have no hydrolipid protective film.

Aging of the lip zone is characterized by increased water loss, loss of volume and changes in syntheses which gives rise to a decrease in dermal density. The progressive reduction in collagens accompanied by the fall in collagen I and collagen III levels is largely responsible for the gradual loss of dermal thickness and hence the decrease in lip volume.

OBJECTS OF THE INVENTION

It is an object of the invention to provide an improved lip balm.

It is another object of the invention to provide a lip balm that aids in the prevention of cracking of the lips.

It is still another object of the invention to provide a lip balm that aids in the healing of cracking of the lips.

Still another object of the invention is to provide a lip balm that aids in giving the lips a smoother look and/or feel.

Yet another object of the invention is to provide a lip balm that aids in giving lips a plumper look and/or feel.

A still further object of the invention is to provide a lip balm in the form of a stick for use in achieving at least one of the foregoing objects of the invention.

Yet an even further object of the invention is to provide a lip balm in the form of a pomade, a cream, or an ointment for achieving at least one of the foregoing objects of the invention.

An even further object of the invention is the inclusion of a medicinal agent in the lip balm of the invention for the treatment or prevention of a medical condition in addition to achieving one or more of the foregoing objects of the invention.

Still other objects of the invention will be appreciated by those of ordinary skill in the art having the benefit of the present disclosure.

SUMMARY OF THE INVENTION

These and other objects of the invention can be realized by the composition set forth in more detail hereinbelow and its use as a lip balm. One aspect of the present invention is an improved lip balm product, comprising a synthetic ceramide; a lip-balm-acceptable anti-irritant compound (preferably alpha-bisabolol); hyaluronic acid and/or sodium hyaluronate, preferably sodium hyaluronate; cosmetic wax (preferably stearyl dimethicone, a particular one being commercially available form Dow Chemical under the name Dow Cosmetic Wax 2503); boswellian oil and/or boswellic acids (and/or their esters and/or their salts); Portulaca extract (preferably whole plant extract); a matrikin-mimetic peptide (preferably palmitoyl tripeptide-38); dehydrated microspheres of marine collagen and glycosaminoglycans; a light diffusing powder (generally a mica or silica); optionally a preservative (preferably selected from Honeysuckle, cosmetically acceptable parabens (such as without limitation methyl paraben, ethyl paraben, propylparaben, butylparaben, isobutylparaben, and heptyl paraben), among others known in the art, such as phenoxyethanol, more preferably honeysuckle; shea butter, and optionally fragrance. The foregoing are formulated in a lip-balm acceptable carrier base formulation which may be any of those known in the art, with a preferred lip-balm carrier base being described more fully below.

Other aspects of the present invention are in the use of the lip balm of the invention to aid in the healing of chapped lips, and/or in aiding the appearance of lips to be full and plumper than would otherwise be the case without the use of such lip balm.

Still another aspect of the present invention is the inclusion in the lip balm of the present invention of medicinal agents known in the an for the treatment and healing of medical conditions of the lips and additional cosmetic agents in order to address additional cosmetic conditions of the lips.

Further objects of the present invention include methods of manufacture of such lip balms.

Yet other objects of the invention will be apparent to those of ordinary skill in the art.

BRIEF DESCRIPTION OF THE DRAWINGS

Not Applicable

DETAILED DESCRIPTION OF THE PREFERRED EMBODIMENT

The invention preferably contains (a) A ceramide, preferably a synthetic ceramide wherein the natural ceramide —C(O)—NH-(1-(2-hydroxyethyl)-2-hydroxyethyl-2yl) linkage between the two long chain hydrocarbon groups has been replaced (such as, without limitation, those in U.S. Pat. No. 5,476,671 (incorporated herein by reference in its entirety) and others) some of which are commercially available from companies such as Symrise, more preferably a cetyihydroxyproline palmitate. Symrepair 153884, available from Symrise, is a combination of this ceramide and the bisabolol component below along with phytosterol and free fatty acids, preferably stearic acid. This and other combinations of ceramides/pseudoceramides with bisabolol are described in US 2010/0286102 (incorporated herein by reference in its entirety), for example, and may be used as suitable alternatives in particular circumstances. When Symrepair is used, it is generally used in amounts (based on the final lip balm formulation) of about 0.5 wt % to about 3.5 wt %, preferably about 0.8 wt % to about 2.5 wt %, more preferably about 2.0 wt %.

(b) An anti-irritant compound, preferably compounds such as alpha-bisabolol, most preferably alpha-bisabolol, where desired, other anti-irritant compounds known for use in lip products by those of ordinary skill in the art may be used in place of or in combination with bisabolol, although alpha-bisabolol is preferred as the anti-irritant compound.

(c) A hyaluronic acid or sodium salt thereof, available from multiple sources, and especially hyaluronic acid (or sodium salts thereof which have been reduced in particle size and homogenized in an oil for greater effectiveness in lip penetration and swelling when contacted with water, such as without limitation, those available from Lipotec (most preferably under the name Hirulip), most preferably this component is sodium hyaluronate (or a sodium hyaluronate that is generated in situ), and in a most highly preferred embodiment, this component is sodium hyaluronate and even more highly preferred in the form of the above mentioned Hirulip from Lipotec. When Hirulip is used, it is generally used in amount (based on the final lip balm formulation) of about 0.5 wt % to about 3.0 wt %, preferably about 1.5 wt % to about 3.0 wt %, more preferably about 2.0 wt %.

(d) cosmetic wax, preferably cosmetic wax 2503 (typically available from Dow Chemical Company as stearyldimethicone in octadecene or in a carrier mixture of octadecene, hexyl-1-decene, butyl-1-tetradecene, ethyl-1-hexadecene, octyldecane, and octyl-decene), the MSDS sheet for Dow Cosmetic Wax 2503 identifying the mixture as 55-75 wt % dimethyl, methyloctadecyl siloxane, 5-10 wt % dimethyl, methyl (branched C18) alkylsiloxane, 7-13 wt % 1-octadene, 3-7 wt % 2-hexyl-1-dodecene, 3-7 wt % 2-butyl-1-tertadecene, 3-7 wt % 2-ethyl-1-hexadecene, 1-5 wt % n-octadecane, and 1-5 wt % 2-octyl-1-decene. When Dow Cosmetic Wax 2503 is used, it is generally used in amounts (based on the final lip balm formulation) of about 5 wt % to about 12 wt %, preferably about 6 wt % to about 9 wt %, more preferably about 8.0 wt %.

(e) boswellian oil (which is a mixture of boswellic acids and other terpenic compounds) and/or one or more boswellic acids. The four major pentacyclic triterpenic acids present in the acidic extract of Boswllia serrate gum resin are:
I) β-Boswellic acid
II) Acetyl-β-Boswellic acid
III) 11-keto-β-Boswellic acid and
IV) Acetyl-11-keto-β-Boswellic acid

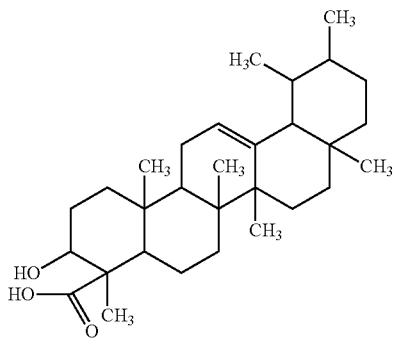

Beta-boswellic acid

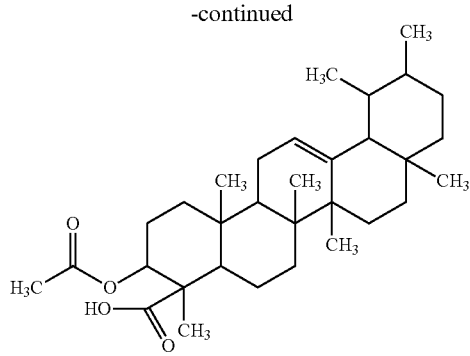

acetyl-beta-boswellic acid

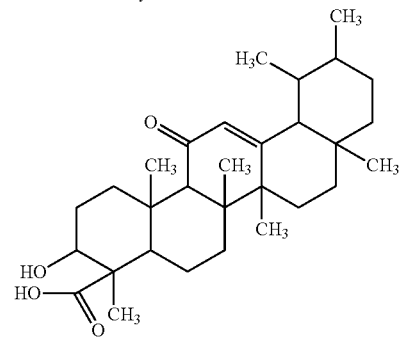

11-keto-Beta-boswellic acid

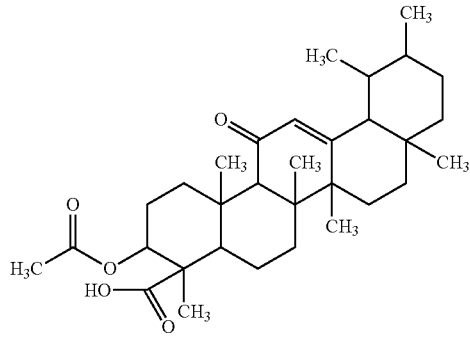

acetyl-11-keto-beta-boswellic acid

In addition, the gum resin includes monterpenes (alpha-thujene), diterpenes (macrocyclic diterpenoids such as incensole, incensole oxide, isoincensole oxide, a diterpene alcohol (serrtol), and triterpese such as alpha and beta amyrins, and tetracyclic triterpenic acids such as tirucall-8,24-diene-21-oic acids. The 4 boswellic acids above have been reported as responsible for the anti-inflammatory action of Boswellin, and of these, the acetyl-11-keto-beta-boswellic acid is reported to be the most potent anti-inflammatory fraction. The Boswellin component is commercially available from Sabinsa Corporation (Piscataway, N.J.). The Boswellian oil is generally used in amounts (based on the final lip balm formulation) of about 0.2 wt % to about 1 wt %, preferably about 0.4 wt % to about 0.7 wt %, more preferably about 0.6 wt %.

(f) extract of the *Portuluca pilosa* plant, most preferably an extract of the entire plant, a commercially available form in combination with the matrikin-mimetic peptide component below is available from Sederma under the name Volulip having the extract and the particular matrikin-mimetic peptide palmitoyl-tripeptide-38 (aka palmitoyl-1-lysyl-dioxymethioninyl-lysine) together with sorbitan isostearate and sucrose cocoate. When Volulip is used, it is generally used in amounts (based on the final lip balm formulation) of from about 0.5 wt % to about 3 wt %, preferably about 1 wt % to about 2.8 wt %, more preferably about 3.5 wt %.

(g) a matrikin-mimetic peptide, preferably palmitoyl tripeptide-38, a palmitoyl-lysyl-dioxymethionyl-lysine.

(h) Dehydrated biodegradable microspheres having pentaerythrityl tetraisostearate, silica dimethyl silylate, sodium chondroitin sulfate and atelocollagen (described more fully in U.S. Pat. No. 5,395,620 (incorporated herein by reference in its entirety) and ex-US counterparts thereof) and commercially available from BASF, under the name of Marine Filling Spheres. The commercially available Marine Filling Spheres are generally used in amounts (based on the final lip balm formulation) of about 1.5 wt % to about 5.5 wt %, preferably about 2 wt % to about 4 wt %, more preferably about 3.5 wt %.

(i) A light diffusing powder such as, without limitation, silica, mica, etc, preferably a silica having titanium dioxide and iron oxide (preferably off white iron oxide or white iron oxide) therewith, a particularly preferable such light diffusing powder being commercially available from Merck, under the name RonaFlair LDP. The light diffusing powder is generally used in amounts (based on the final lip balm formulation) of about 1 wt % to about 6.5 wt %, preferably about 2 wt % to about 4 wt %, more preferably about 3.0 wt %.

The above active ingredients are provided in a base medium of oils and waxes, optionally with fragrances and moisturizers added to provide a more consumer-friendly product.

One component of the invented lip balm product is preferably a synthetic ceramide. Natural ceramides are compounds having two long chain hydrocarbon groups linked together via a —C(O)—NH-(1-(2-hydroxyethyl)-2-hydroxyethyl-2-yl) bridge. Skin tissue has a protective layer referred to as a lipid bilayer, which helps bind corneocytes to protect skin tissue from external damage. The lipid bilayer is itself comprised of ceramides, fatty acids and cholesterol. Skin tissue with decreased ceramide levels have been shown to suffer a variety of damage, but unlike fatty acids and cholesterol, ceramides cannot be easily replaced. As such, while the natural ceramides may be used in the present invention, they are preferably synthetic ceramides in which the natural linkage referred to above has been replaced The synthetic ceramides for use in the invention have the natural linkage referred to above replaced as in (without limitation) those synthetic ceramides described more fully in U.S. Pat. No. 5,476,671 (incorporated herein in its entirety by reference) some of which are commercially available from companies such as Symrise, more preferably the synthetic ceramide is cetylhydroxyproline palmitate. In some embodiments one or more of an anti-irritant lip-balm acceptable compound which may be known in the art (such as without limitation, alpha-bisabolol or non-steroidal anti-inflammatory compounds), phytosterols (such as without limitation rapeseed sterols), and free fatty acids (such as without limitation stearic acid) may be used with the ceramide to help supplement the lipid bilayer of the skin tissue. In some commercially available ceramide products, one or more of these supplemental agents are part of the commercially available ceramide formulation. While the ceramide may be used without these supplemental agents present, in a preferred embodiment these supplemental agents are present in the final formulation of the lip balm and are discussed more fully below. One non-limiting, but preferable, commercially available version of the synthetic ceramide is available from Symrise under the name SYMREPAIR, and is described is also described in US 2001/0286102 (incorporated herein in its entirety by reference. The ceramide is generally used in a concentration range of about 0.005 wt % to about 0.175 wt %, preferably about 0.008 wt % to about 0.125 wt %, more preferably about 0.02 wt % to about 0.10 wt % (each based on the entire formulation).

A second component of the invented lip balm is an optionally present, but preferably present, anti-irritant compound. It may be selected from non-steroidal anti-inflammatory agents known in the art, but is preferably alpha-bisabolol. When present, it is present up to a total lip balm formulation amount of up to 0.475 wt %, preferably up to 0.425 wt %, more preferably up to 0.4 wt %, even more preferably up to 0.375 wt %, yet more preferably, up to 0.325 wt %, even more preferably up to 0.3 wt % (each inclusive of the endpoint stated). Other particularly useful concentrations of this component include, without limitation, ranges having one of the above upper limits and one of the following as a lower limit about 0.005 wt %, about 0.008 wt %, about 0.02 wt %, about 0.10 wt %, about 0.105 wt %, about 0.108 wt %, about 0.12 wt %, about 0.125 wt %, about 0.175 wt %, about 0.20 wt %, about 0.205 wt %, about 0.208 wt %, about 0.22 wt %, about 0.225 wt %, about 0.275 wt %, about 0.30 wt %, about 0.305 wt %, about 0.308 wt %, about 0.32 wt %, about 0.325 wt %, about 0.375 wt %, about 0.40 wt %, about 0.425 wt %, and about 0.475 wt %. Each of the above upper or lower limit points are also considered individual preferred concentrations independent of the ranges constructed therefrom.

A third component of the invented lip balm product are small particles of sodium hyaluronate. Skin tissue, including lip tissue, contains hyaluronic acid, a natural polymer. Hyaluronic acid maintains tissue hydration and helps retain water within the skin tissue. Sodium hyaluronate particles penetrate the lip tissue, and increase in size by absorbing moisture from the lip tissue as well as external moisture. The swelling of the sodium hyaluronate particles increase the volume of the lip tissue, reducing wrinkles and plumping the lips. Preferably, the sodium hyaluronate particles are delivered in an oil-based suspension to prevent particle expansion before penetration into the lip tissue. A commercially available version is Hirulip (available from Lipotec). The sodium hyaluronate is present in the final lip balm formulation in an amount of about 0.0045 wt % to about 0.033 wt %, preferably about 0.013 wt % to about 0.033 wt %, more preferably about 0.018 wt % to about 0.022 wt %.

A fourth component is the cosmetic wax as described above, most preferably Cosmetic Wax 2503 (available from Dow). Cosmetic Wax 2503 is described as stearyldimethicone in octadecene or in a carrier mixture of octadecene, hexyl-1-decene, butyl-1-tetradecene, ethyl-1-hexadecene, octyldecane, and octyl-decene), the MSDS sheet for Dow Cosmetic Wax 2503 identifying the mixture as 55-75 wt % dimethyl, methyloctadecyl siloxane, 5-10 wt % dimethyl, methyl (branched C18) alkylsiloxane, 7-13 wt % 1-octadene, 3-7 wt % 2-hexyl-1-dodecene, 3-7 wt % 2-butyl-1-tertadecene, 3-7 wt % 2-ethyl-1-hexadecene, 1-5 wt % n-octadecane, and 1-5 wt % 2-octyl-1-decene. Alternative cosmetic waxes for use as this component include fatty (straight or branched)alkyldimethicones (i.e., di($C_{1-4}$alkyl), $C_{1-4}$alkyl $C_{12-22}$(straight or branched alkyl) siloxane, preferably the $C_{1-4}$ alkyl groups being selected independently from methyl and ethyl, more preferably each of the $C_{1-4}$ alkyl groups being methyl, and preferably the $C_{12-22}$(straight or branched alkyl) group being of 14-20, more preferably of 16-18, still more preferably of 18 carbons. In the final lip balm formulation, the fatty (straight or branched)alkyldimethicones is present an amount of about 3.0 wt % to about 10.2 wt %, preferably about 3.6 wt % to about 7.65 wt %, more preferably about 4.8 wt % to about 6.8 wt %. In a preferred embodiment this is made up of a mixture of fatty (straight)alkyldimethicones and fatty (branched)alkyldimethicones where the straight chain version is present in 55-75 parts by weight relative to 5-10 parts by weight of the branched version.

A fifth component is boswellian oil and/or boswellic acids or salts or esters thereof, as described more fully above. The boswellian oil is used in the instant lip balm formulation in an amount based on the final lip-balm of about 0.2 wt % to about 1.0 wt %, preferably about 0.4 wt % to about 0.7 wt % and more preferably about 0.6 wt %.

A sixth component of the invented lip balm product is a compound of an extract of the *Portuluca pilosa* plant in combination with a peptide. The *Portuluca pilosa* plant, also known as "Kiss-Me-Quick," is part of the purslane family of edible plants." This component combines an extract of the whole plant *Portuluca pilosa* in combination with a matrikin-mimetic peptide for the purposes of restoring lip volume and firmness, although for use in the present invention, they may be added as separate components. The peptide is preferably a palmitoyl-peptide 38, i.e., palmitoyl-lysyl-dioxymethionyl-lysine. The *Portuluca pilosa* plant extract with the matrikin-mimetic peptide (palmitoyl-$KMO_2K$) is available from Sederma under the name Volulip. The Portulaca Extract is generally used in an amount such that the final concentration in the instant lip balm is about 0.01 wt % to about 0.06 wt %, preferably about 0.02 wt % to about 0.056 wt %, more preferably about 0.04 wt %. The tripeptide-38 is present in the final formulation in an amount of about 0.00025 wt % to about 0.0015 wt %, preferably about 0.0005 wt % to about 0.0014 wt %, more preferably about 0.001 wt %

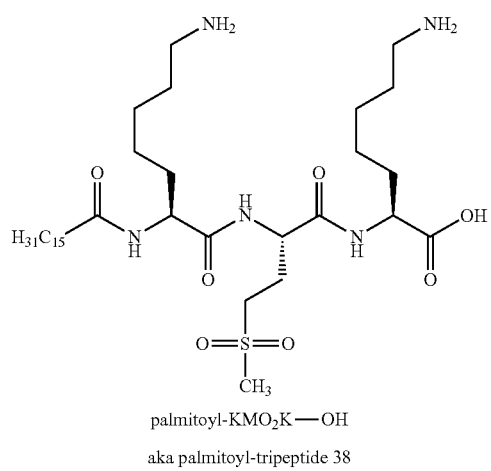

palmitoyl-$KMO_2K$—OH aka palmitoyl-tripeptide 38

A seventh component of the invented lip balm product is dehydrated microspheres of marine collagen and glycosaminoglycans. These microspheres have the capacity to rehydrate in the presence of water and regain their initial volume. While dehydrated, the microspheres are small enough to penetrate crevices in lips. The microspheres increase in size through absorption of moisture in the lips, which causes a smoothing of the lip surface. The microspheres are slowly degraded by enzymes in the lip, which allows the microspheres to release the moisture initially absorbed from the lips, returning the moisture to the lips. The microspheres are preferably comprised of marine atelocollagen and marine chrondroitin sulfate, as disclosed in U.S. Pat. Nos. 5,395,620, 5,420,248 and 5,622,656, as well as non-US counterparts (all incorporated herein by reference in their entirety). A commercially available form can be obtained from BASF under the name Marine Filling Spheres. The Marine Filling Spheres are used in an amount based on the entire lip balm composition of about 1.5 wt % to about 5.5 wt %, preferably about 2.0 wt % to about 4.0 wt %, more preferably about 2.0 wt %, resulting in a sodium chondroitin sulfate content in the final lip balm formulation of about 0.009 to about 0.033, preferably about 0.012 wt % to about 0.024 wt %, more preferably about 0.021 wt % and in an atelocollagen content of the final lip balm of about 0.0045 to about 0.0165 wt %, preferably about 0.06 wt % to about 0.012 wt %, more preferably about 0.0105 wt %.

An eighth component is a light diffusing powder, such as mica or silica preferably that also contains titanium dioxide, and iron oxide (preferably off white iron oxide or white iron oxide) so as to help fill wrinkles and create an even diffuse light distribution. The particles of most desirable use are those which are essentially spherical and yield an essentially instant smooth look and feel. A non-limiting, but preferred, commercially available form of the silica light diffusing powder is available under the name Ronaflair LDP from Merck. The light diffusing powder is typically used in an amount based on the entire lip balm formulation of about 1 wt % to about 6.5 wt %, preferably about 1.5 wt % to about 4.5 wt %, most preferably about 3.0 wt %. When the light diffusing powder contains the titanium dioxide and or the iron oxide in addition to either or both of silica and/or mica, the silica (alone) or mica (alone) or combined silica and mica (if both are present) content of the final lip balm formulation is about 0.74 wt % to about 5.525 wt %, preferably about 1.11 wt % to about 3.825 wt %, more preferably about 2.22 wt % to about 2.55 wt %; the titanium dioxide content is preferably about 0.15 wt % to about 1.56 wt %, more preferably about 0.225 wt % to about 1.08 wt %, still more preferably 0.45 wt % to about 0.72 wt %, and the iron oxides, when present, are present in amounts based on the final lip balm formulation of less than 0.02 wt % to less than 0.13 wt %, more preferably less than 0.03 wt % i to less than 0.009 wt %, still more preferably less than 0.06 wt %. Alternative ranges; for the iron oxide content, when present include: from about 0.02 wt % to less than 0.13 wt %, more preferably from about 0.03 wt % to less than 0.009 wt %, still more preferably about 0.06 wt %.

A ninth component, which is optional, but preferably present, is a preservative, which may be selected from honeysuckle, various parabens, butylene glycol, and phenoxyethanol. Preferably, honeysuckle is the preservative, but small amounts of one or more of the others mentioned may be present due to their potential inclusion in one of more of the commercially available materials mentioned in the eight components discussed above. The honeysuckle, when present is generally present in an amount of about 0.002 wt % to about 0.2 wt %, preferably about 0.1 wt % based on the final lip balm formulation. Generally, if present, phenoxyethanol is present in an amount, based on the final lip balm formulation of (a) about 0.0045 wt % to about 0.033 wt %, about 0.013 wt % to about 0.033 wt %, or about 0.18 wt % to about 0.022 wt % (b) about 0.010875 to about 0.039875 wt %, preferably about 0.02455 wt % to about 0.029 wt %, more preferably about 0.025375 wt %, (c) a combination of an amount from the foregoing group (a) ranges and an amount form the foregoing group (b) ranges so that new ranges are described having
- (1) a lower limit selected from either the lower limit of a group (a) range or the lower limit of a group (b) range or the sum of a lower limit of a group (a) range and a lower limit of a group (b) range and
- (2) an upper limit selected from a group (a) range upper limit, a group (b) range upper limit or the sum of a group (a) range upper limit and group (b) range upper limit.

Generally when butylene glycol is present, it is present based on the final lip balm formulation in an amount of about 0.015 wt % to about 0.055 wt %, preferably about 0.02 wt % to about 0.04 wt %, more preferably about 0.035 wt %. When parabens are present, they are generally present (as a group) in an amount of about 0.0041 wt % to about 0.0151 wt %, preferably about 0.0055 wt % to about 0.011 wt %, more preferably about 0.00965 wt %. When present the parabens are preferably one or more of methyl paraben, ethyl paraben, propyl paraben, butyl paraben, butyl paraben, and isobutyl paraben. In some embodiments each of these are present. When present, the more preferred ranges for the individual parabens are independently for methyl paraben about 0.0023 wt % to about 0.008535 wt %, more preferably about 0.0031 wt % to about 0.0062 wt %, still more preferably about 0.00543 wt %; for ethyl paraben about 0.0006 wt % to about 0.0022 wt %, more preferably about 0.0008 wt % to about 0.0016 wt %, still more preferably about 0.0014 wt %; for propyl paraben about 0.0003 wt % to about 0.0011 wt %, more preferably 0.0004 wt % to about 0.0008 wt %, still more preferably about 0.0007 wt %; for butyl paraben about 0.0006 wt % to about 0.0022 wt %, more preferably about 0.0008 wt % to about 0.0016 wt %, still more preferably about 0.0014 wt %; and for isobutyl paraben about 0.0003 wt % to about 0.0011 wt %, more preferably 0.0004 wt % to about 0.0008 wt %, still more preferably about 0.0007 wt %.

Turning to the (independently) optional, but preferably present (most preferably all present), ingredients for the lip balm base, these include:

sweet almond oil in an amount based on the final lip balm formulation of about 10 wt % to about 20 wt %, preferably about 15.5 wt %;

castor oil in an amount based on the final lip balm formulation of about 10 wt % to about 20 wt %, preferably about 14.8 wt %;

beeswax in an amount based on the final lip balm formulation of about 5.0 wt % to about 12 wt %, preferably about 9.0 wt %;

paraffin wax in an amount based on the final lip balm formulation of about 5.0 wt % to about 12 wt %, preferably 9.0 wt %;

cetyl palmitate in an amount based on the final lip balm formulation of about 3.0 wt % to about 7.0 wt %, preferably about 5.0 wt %;

cetearyl alcohol in an amount based on the final lip balm formulation of about 3.0 wt % to about 7.0 wt %, preferably about 4.9 wt %;

candelilla wax in an amount based on the final lip balm formulation of about 0.5 wt % to about 1.2 wt %, preferably about 0.8 wt %;

ozokerite in an amount based on the final lip balm formulation of about 2.0 wt % to about 4.0 wt %, preferably about 2.8 wt %;

free fatty acid, preferably stearic acid, in addition to any such free fatty acid present as a partial carrier in the active agents as commercially available above, in an amount based on the final lip balm formulation of about 0.2 wt % to about 1.0 wt %, preferably about 0.15 wt % and when inclusive of the partial carrier amounts mentioned above generally have an additional amount of about 0.005 wt % to about 0.175 wt %, preferably an additional amount of about 0.008 wt % to about 0.125 wt %, and more preferably an additional amount of about 0.002 wt % to about 0.10 wt %;

shea butter in an amount based on the final lip balm formulation of about 0.2 wt % to about 1.0 wt %, preferably about 015 wt %;

$C_{12-15}$ alkyl benzoate in an amount based on the final lip balm formulation of about 4.0 wt % to about 8.0 wt %, preferably about 6.0 wt %

Tridecyl trimellitate in an amount based on the final lip balm formulation of about 2.0 wt % to about 6.0 wt %, preferably about 4.0 wt %;

Cetyl alcohol in an amount based on the final lip balm formulation of about 1.0 wt % to about 5.0 wt %, preferably about 3.0 wt %;

Petrolatum, preferably white petrolatum, in an amount based on the final lip balm formulation of about 1.0 wt % to about 3.0 wt %, preferably about 2.0 wt %;

optionally fragrance, which if present is generally present up to an amount based on the final lip balm formulation of about 1.2 wt %, and preferably is present in an amount of about 0.4 wt % to about 1.2 wt %, more preferably about 0.8 wt %, and alpha-bisabolol, in amounts as described above, whether or not it is included as part of the active ingredients described above.

Turning to the further optional components, each of which is independently optional (and may be part of the base carrier or subcomponents in whole or in part of commercially available formulations of one or more of the active agents described above) and may be present in amounts below the ranges stated, but if present are preferably within the ranges stated here. In a particularly preferred embodiment each is present. These include:

phytosterols, preferably rapeseed sterols, and when present are present in amounts of about 0.0005 wt % to about 0.035 wt %, preferably 0.008 wt % to about 0.025 wt %, more preferably 0.002 wt % to about 0.02 wt %;

hexadecanol in an amount based on the final lip balm formulation of about 0.42 wt % to about 3.40 wt %, more preferably about 0.672 wt % to about 2.43 wt %, more preferably about 1.68 wt % to about 1.938 wt %;

isohexadecane in an amount based on the final lip balm formulation of about 0.41 wt % to about 2.60 wt %, more preferably about 1.25 wt % to about 2.60 wt %, still more preferably bout 1.66 wt % to about 1.73 wt %;

tripeptide-1 in an amount based on the final lip balm formulation of about 0.0002 wt % to about 0.0017 wt %; preferably about 0.00067 wt % to about 0.0017 wt %, more preferably about 0.0009 wt % to about 0.0011 wt %;

bis PEG-/PEG-14/14 dimethicone in an amount based on the final lip balm formulation of about 0.02 wt % to about 0.17 wt %, more preferably about 0.13 wt % to about 0.17 wt %, still more preferably about 0.09 wt % to about 0.11 wt %;

ethylene/propylene/styrene copolymer in an amount based on the final lip balm formulation of about 0.013 to about 0.099 wt %, preferably about 0.04 wt % to about 0.1 wt %, more preferably about 0.05 wt % to about 0.065 wt %;

butylene/ethylene/styrene copolymer in an amount based on the final lip balm formulation of about 0.013 to about 0.099 wt %, preferably about 0.04 wt % to about 0.1 wt %, more preferably about 0.05 wt % to about 0.065 wt %;

cyclopentasiloxane in an amount based on the final lip balm formulation of about 0.0045 wt % to about 0.034 wt %, preferably about 0.013 wt % to about 0.034 wt %, more preferably about 0.18 wt % to about 0.023 wt % xanthan gum in an amount based on the final lip balm formulation of about 0.004 wt % to about 0.034 wt %, preferably about 0.013 wt % to about 0.034 wt %; more preferably about 0.018 wt % to about 0.023 wt %;

1-octadecene in an amount based on the final lip balm formulation of about 0.35 wt % to about 1.56 wt %, preferably about 0.42 wt % to about 1.17 wt %, more preferably about 0.56 wt % to about 1.04 wt %;

2-hexyl-1-dodecene in an amount based on the final lip balm formulation of about 0.15 wt % to about 0.84 wt %, preferably about 0.18 wt % to about 0.63 wt %, more preferably about 0.24 wt % to about 0.56 wt %;

2-butyl-1-tetradecene in an amount based on the final lip balm formulation of about 0.15 wt % to about 0.84 wt %, preferably about 0.18 wt % to about 0.63 wt %, more preferably about 0.24 wt % to about 0.56 wt %;

2-ethyl-hexadecene in an amount based on the final lip balm formulation of about 0.15 wt % to about 0.84 wt %, preferably about 0.18 wt % to about 0.63 wt %, more preferably about 0.24 wt % to about 0.56 wt %;

n-octadecane in an amount based on the final lip balm formulation of about 0.05 wt % to about 0.6 wt %, preferably about 0.06 wt % to about 0.45 wt %, more preferably about 0.08 wt % to about 0.4 wt %;

octyl-1-decene in an amount based on the final lip balm formulation of about 0.05 wt % to about 0.6 wt %, preferably about 0.06 wt % to about 0.45 wt %, more preferably about 0.08 wt % to about 0.4 wt %;

one or both of (a) cetearyl ethylhexanoate in an amount based on the final lip balm formulation of about 0.44 wt % to about 2.69 wt %, preferably about 0.89 wt % to about 2.51 wt %, more preferably about 3.134 wt % and/or (b) pentaerythrityl tetraisostearate in an amount based on the final lip balm formulation of about 1.41 wt % to about 5.18 wt %, preferably about 1.88 wt % to about 3.77 wt %, more preferably about 3.29 wt %;

sorbitan isostearate in an amount based on the final lip balm formulation of about 0.04 wt % to about 0.24 wt %, preferably about 0.08 wt % to about 0.224 wt %, more preferably about 0.16 wt %;

sucrose cocoate in an amount based on the final lip balm formulation of about 0.002 wt % to about 0.012 wt %, preferably about 0.004 wt % to about 0.0112 wt, more preferably about 0.008 wt %;

ethylhexyl palmitate in an amount based on the final lip balm formulation of about 1.41 wt % to about 5.18 wt %, preferably about 1.88 wt % to about 3.77 wt %, more preferably about 3.29 wt %; and silica dimethylsilicate in an amount based on the final lip balm formulation of about 0.045 wt % to about 0.165 wt %, preferably about 0.06 wt % to about 0.12 wt %, more preferably about 0.105 wt %;

The following tables set out various non-limiting embodiments of the present invention. Those of ordinary skill in the art will readily appreciate alternatives for particular elements in the tables and the corresponding elements thereto.

More specifically, Table 1 sets out a preferred listing of active ingredients, and Table 2 sets out an optional listing, but a preferred listing of the inactive ingredients. Table 3 lists some additional optional inactive ingredients, which may or may not be present depending on whether they are present as carriers for the active ingredients or are simply desirable to be present. In one embodiment, these optional components in Table 3 are all absent, in another, these optional components in Table 3 are all present. In yet other embodiments, some of the optional components of Table 3 are present while others are absent. Table 4 presents ranges, preferred ranges, a most preferred concentrations with respect to the inactive agents mentioned in Table 2 and one may independently select the general range, preferred range, or specific amount for each component separately. Table 5 shows some particular embodiment of the present invention, with both suitable ranges and preferred amounts of the active agents numbered 1-7 and preferred amounts for the remaining ingredients.

TABLE 1

| Active ingredients |
|---|
| ceramide (preferably synthetic ceramide) |
| anti-irritant compound (preferably bisabolol) |
| sodium hyaluronate |
| cosmetic wax (preferably cosmetic wax 2503) |
| boswellian oil |
| extract of the *Portuluca pilosa* plant |
| matrikin-mimetic peptide, preferably palmitoyl tripeptide-38 |
| dehydrated microspheres of marine collagen and glycosaminoglycans |
| light diffusing powder |

TABLE 2

| Inactive ingredients |
|---|
| sweet almond oil |
| castor oil |
| beeswax |
| paraffin wax |
| cetyl palmitate |
| cetearyl alcohol |
| candelilla wax |
| ozokerite |
| stearic acid |
| shea butter |
| C12-15 alkyl benzoate |
| tridecyl trimellitate |
| cetyl alcohol |
| petrolatum |
| fragrance |
| Preservative, preferably honeysuckle |

TABLE 3

| |
|---|
| Phytosterol |
| Hexadecanol |
| Sucrose cocoate |
| Sorbitan isostearate |
| 1-Octadecene |
| 2-Hexyl-1-dodecene |
| 2-Butyl-1-tetradecene |
| 2-Ethyl-1-hexadecene |
| n-Octadecane |
| Octyl-1-decene |
| cetearyl ethylhexanoate and/or Penterythritol tetraisostearate |
| Ethylhexyl palmitate |
| Silica dimethylsilicate |
| isohexadecane |
| Bis Peg/PEG14/14-dimethicone |
| Ethylene/propylene/styrene copolymer |
| Butylene/ethylene/stryrene copolymer |
| cyclopentasiloxane |
| phenoxyethanol |

TABLE 3-continued

Tripeptide-1
Xanthan gum
Cetearyl ethylhexanoate
Silica and/or mica
Titanium dioxide
Iron oxide

TABLE 4

| ingredient | Wt % | preferred wt % |
|---|---|---|
| sweet almond oil | 10-20 | 15.5 |
| castor oil | 10-20 | 14.8 |
| beeswax | 5-12 | 9.0 |
| paraffin wax | 5-12 | 9.0 |
| cetyl palmitate | 3-7 | 5.0 |
| cetearyl alcohol | 3-7 | 4.9 |
| candelilla wax | 0.5-1.2 | 0.8 |
| ozokerite | 2-4 | 2.8 |
| stearic acid* | 0.2-1 | 0.5 |
| shea butter | 0.2-1 | 0.5 |
| C12-15 alkyl benzoate | 4-8 | 6.0 |
| tridecyl trimellitate | 2-6 | 4.0 |
| cetyl alcohol | 1-5 | 3.0 |
| petrolatum | 1-3 | 2.0 |
| fragrance | 0.4-1.2 | 0.8 |
| Preservative, preferably honeysuckle | 0.02-0.2 | 0.1 |

*in addition to any amounts of free fatty acids present in the commercially available components in Table 1 actually used

TABLE 5

| Ingr. No. | ingredient | General range Wt % (about) | preferred wt % (about) |
|---|---|---|---|
| 1 | Symrepair (Ceramides/anti-irritant) | 0.5 to 3.5 | 2.0 |
| 2 | Hilurlip | 0.5 to 3.0 | 2.0 |
| 3 | Dow Corning cosmetic wax 2503 | 5 to 12 | 8.0 |
| 4 | boswellian oil | 0.2 to 1 | 0.6 |
| 5 | Volulip (Extract of *Portuluca* plant with matrikin-mimetic peptide) | 0.5 to 3 | 2.0 |
| 6 | Marine Filling Spheres (Dehydrated microspheres of marine collagen and glycosaminoglycan) | 1.5 to 5.5 | 3.5 |
| 7 | light diffusing powder | 1 to 6.5 | 3.0 |
| 8 | honey suckle | | 0.1 |
| 9 | sweet almond oil | | 15.5 |
| 10 | castor oil | | 14.8 |
| 11 | beeswax | | 9.0 |
| 12 | paraffin wax | | 9.0 |
| 13 | cetyl palmitate | | 5.0 |
| 14 | cetearyl alcohol | | 4.9 |
| 15 | candelilla wax | | 0.8 |
| 16 | ozokerite | | 2.8 |
| 17 | stearic acid* | | 0.5 |
| 18 | Alphabisabolol** | | 0.2– |
| 19 | shea butter | | 0.5 |
| 20 | C12-15 alkyl benzoate | | 6.0 |
| 21 | tridecyl trimellitate | | 4.0 |
| 22 | cetyl alcohol | | 3.0 |
| 23 | petrolatum | | 2.0 |
| 24 | fragrance | | 0.8 |
| | | | 100.0 |

*in addition to free fatty acid content of Symrepair
**in addition to anti-irritant content of Symrepair.

Using the components as stated in Table 5, a lip balm of the invention is prepared as follows:

a. Separately prepare mixtures of Phase A Components, Phase B Components, and Phase C Components where Phase A Components are Ingredients Nos. 9-17 and 22, Phase B Components are Ingredients Nos. 18-21 and 23, and Phase C Components are Ingredient Nos. 1-8 and 24.

b. Heat the Phase A Component mixture to a first temperature of about 80° C. to about 85° C. (preferably about 82° C.) until the Phase A Components are completely melted.

c. When the Phase A components are completely melted (preferable as soon as they are completely melted), begin cooling the blend until a second temperature of about 72° C. to about 78° C. (preferably about 75° C.).

d. Begin adding the Phase B Component mixture when the Phase A mixture has reached the second temperature.

e. Continue cooling the Phase A and Phase B mixture until a third temperature of about 50° C. to about 65° C. (preferably about 58° C.).

f. Add the Phase C Component mixture when the temperature has reached the third temperature.

g. Allow the completed blend to cool to room temperature.

After all of the components are added and the complete mixture is continuing to cool, the mixture can be placed into containers or molds as desired to form the final product.

As an alternative to the previous paragraph, the Phase A components need not be premixed but can be added in series (or a series of partial mixtures of some of the Phase A ingredients) to a heating vessel either before or during the heating operation. As an independent alternative to the serial addition, the Phase B ingredients need not be premixed before adding to the melted phase A Component, but may be added as either a series of partial mixtures or a series of individual ingredient additions, so long as they are added at the appropriate temperature ranges. As still another independent alternative, the Phase C Component ingredients need not be prepared as a preblend before adding to the Phase A+Phase B combination, but may be added serially either as individual components or a series of mixtures of less than all of the Phase C Component ingredients. In each of these alternatives, one may have some partial mixtures and some individual ingredients as desired rather than a full mixture of the Phase A Components, Phase B Components, and/or Phase C Components respectively. Nonetheless, preblends of the entire Phase A Components, Phase B Components, and Phase C Components offer the advantage of a better assurance of uniformity of having all of the ingredients throughout the final lip balm composition.

While certain novel features of the present invention have been shown and described, it will be understood that various omissions, substitutions and changes in the forms and details of the device illustrated and in its operation can be made by those skilled in the art without departing from the spirit of the invention.

We claim:

1. A cosmetic composition for healing cracked lips consisting essentially of
   0.5-3.5% synthetic ceramide,
   0.5-3% sodium hyaluronate,
   0.2-1% boswellian oil,
   0.5-3% Portuluca pilosa extract,
   0.00025-0.0015% palmitoyl tripeptide 38,
   1.5-5.5% dehydrated microspheres of marine collagen and glycosaminoglycans,
   10-20% sweet almond oil, 10-20 castor oil,
5-12% beeswax,
5-12% paraffin wax,
3-7% cetyl palmitate,
3-7% cetyl alcohol,
0.5-1.2% candelilla wax,
2-4% ozokerite,
0.2-1% stearic acid,
0.1-0.3% alphabisobolol,
0.2-1% shea butter,
2-6% tridecyl trimellitate, and
1-3% petroleum, said percentages expressed as weight percent.

2. A cosmetic composition for healing cracked lips consisting essentially of
0.5-3.5% synthetic ceramide,
0.5-3% sodium hyaluronate,
0.2-1% boswellian oil,
0.5-3% Portuluca pilosa extract,
0.00025-0.0015% palmitoyl tripeptide 38,
1.5-5.5% dehydrated microspheres of marine collagen and glycosaminoglycans,
10-20% sweet almond oil,
10-20 castor oil,
5-12% beeswax,
5-12% paraffin wax,
3-7% cetyl palmitate,
3-7% cetyl alcohol,
0.5-1.2% candelilla wax,
2-4% ozokerite,
0.2-1% stearic acid,
0.1-0.3% alphabisobolol,
0.2-1% shea butter,
2-6% tridecyl trimellitate,
1-3% petroleum; and
one or more members selected from the group consisting of
5 to 12% stearyldimethicone in an octadecene carrier,
1 to 6.5% mica,
1 to 6.5% silica,
4 to 8% C12-15 alkyl benzoate, and
0.02 to 0.2% honeysuckle, said percentages expressed as weight percent.

* * * * *